(12) United States Patent
Forster et al.

(10) Patent No.: US 8,585,594 B2
(45) Date of Patent: Nov. 19, 2013

(54) METHODS OF ASSESSING INNER SURFACES OF BODY LUMENS OR ORGANS

(75) Inventors: David C. Forster, Los Altos Hills, CA (US); Brian Beckey, Woodside, CA (US); Brandon Walsh, Syracuse, UT (US); Scott Heneveld, Whitmore, CA (US)

(73) Assignee: Phoenix Biomedical, Inc., Petoskey, MI (US)

( * ) Notice: Subject to any disclaimer, the term of this patent is extended or adjusted under 35 U.S.C. 154(b) by 1279 days.

(21) Appl. No.: 11/420,189

(22) Filed: May 24, 2006

(65) Prior Publication Data

US 2008/0009746 A1 Jan. 10, 2008

(51) Int. Cl.
*A61B 8/00* (2006.01)

(52) U.S. Cl.
USPC ........... 600/437; 600/407; 600/443; 600/459; 600/473; 600/476; 623/1.1; 623/1.24; 623/1.26

(58) Field of Classification Search
USPC ................. 623/1.1, 1.24, 1.26, 1.3, 2.1–2.42, 623/901–904, 910, 913; 600/437, 443, 459, 600/462, 466, 467, 470, 481, 485, 498
See application file for complete search history.

(56) References Cited

U.S. PATENT DOCUMENTS

| 376,531 A | 1/1888 | Byrnes |
|---|---|---|
| 1,314,601 A | 9/1919 | McCaskey |
| 3,579,642 A | 5/1971 | Hefferman |
| 3,587,115 A | 6/1971 | Shiley |
| 3,657,744 A | 4/1972 | Ersek |
| 3,661,148 A | 5/1972 | Kolin |
| 3,671,979 A | 6/1972 | Moulopoulos |
| 3,755,823 A | 9/1973 | Hancock |
| 3,867,728 A | 2/1975 | Stubstad et al. |
| 4,056,854 A | 11/1977 | Boretos et al. |
| 4,106,129 A | 8/1978 | Carpentier et al. |
| 4,328,839 A | 5/1982 | Lyons et al. |
| 4,339,831 A | 7/1982 | Johnson |

(Continued)

FOREIGN PATENT DOCUMENTS

| WO | WO 91/17730 | 11/1991 |
|---|---|---|
| WO | WO 99/33414 | 7/1999 |

(Continued)

OTHER PUBLICATIONS

U.S. Appl. No. 11/066,126—Office Action, Oct. 16, 2008.

(Continued)

*Primary Examiner* — James Kish
(74) *Attorney, Agent, or Firm* — Mark Stirrat; One LLP

(57) ABSTRACT

Devices and methods for assessing the size, shape, and topography of vessel lumens and hollow portions of organs are described. The devices and methods are particularly adapted for determining the size, shape, topography, and compliance of the native heart valves to facilitate the later implantation of a prosthetic heart valve. The devices are typically catheter-based having an assessment mechanism fixed to a distal end of the catheter. The assessment mechanism generally includes an expandable member, such as a balloon. The assessment mechanism may also include an imaging member, a physical assessment member, an electronic mapping construction, an alignment mechanism, a valvuloplasty balloon, or any combinations thereof. The methods typically comprise deploying the balloon percutaneously to a target location, expanding the balloon, and determining one or more physical parameters associated with the target location.

9 Claims, 10 Drawing Sheets

(56) References Cited

U.S. PATENT DOCUMENTS

| | | |
|---|---|---|
| 4,340,091 A | 7/1982 | Skelton et al. |
| 4,624,822 A | 11/1986 | Arru et al. |
| 4,683,883 A | 8/1987 | Martin |
| 4,692,165 A | 9/1987 | Bokros |
| 4,758,151 A | 7/1988 | Arru et al. |
| 4,777,951 A | 10/1988 | Cribier et al. |
| 4,796,629 A | 1/1989 | Grayzel |
| 4,819,751 A | 4/1989 | Shimada et al. |
| 4,822,345 A | 4/1989 | Danforth |
| 4,822,353 A | 4/1989 | Bokros |
| 4,856,516 A | 8/1989 | Hillstead |
| 4,878,906 A | 11/1989 | Lindemann et al. |
| 4,881,547 A | 11/1989 | Danforth |
| 4,909,252 A | 3/1990 | Goldberger |
| 4,960,424 A | 10/1990 | Grooters |
| 4,986,830 A | 1/1991 | Owens et al. |
| 4,994,077 A | 2/1991 | Dobben |
| 5,002,567 A | 3/1991 | Bona et al. |
| 5,009,662 A | 4/1991 | Wallace et al. |
| 5,037,434 A | 8/1991 | Lane |
| 5,059,177 A | 10/1991 | Towne et al. |
| 5,078,737 A | 1/1992 | Bona et al. |
| 5,098,374 A | 3/1992 | Othel-Jacobsen et al. |
| 5,123,919 A | 6/1992 | Sauter et al. |
| 5,163,953 A | 11/1992 | Vince |
| 5,163,954 A | 11/1992 | Curcio et al. |
| 5,213,580 A | 5/1993 | Slepian et al. |
| 5,238,454 A | 8/1993 | Schmidt |
| 5,240,004 A | 8/1993 | Walinsky et al. |
| 5,273,537 A | 12/1993 | Haskvitz et al. |
| 5,326,371 A | 7/1994 | Love et al. |
| 5,328,471 A | 7/1994 | Slepian |
| 5,352,199 A | 10/1994 | Tower |
| 5,370,685 A | 12/1994 | Stevens |
| 5,397,308 A | 3/1995 | Ellis et al. |
| 5,397,348 A | 3/1995 | Campbell et al. |
| 5,397,351 A | 3/1995 | Pavcnik et al. |
| 5,403,305 A | 4/1995 | Sauter et al. |
| 5,411,552 A | 5/1995 | Andersen et al. |
| 5,423,886 A | 6/1995 | Arru et al. |
| 5,443,474 A | 8/1995 | Sfakianos et al. |
| 5,454,838 A | 10/1995 | Vallana et al. |
| 5,522,885 A | 6/1996 | Love et al. |
| 5,531,094 A | 7/1996 | More et al. |
| 5,545,209 A | 8/1996 | Roberts et al. |
| 5,545,214 A | 8/1996 | Stevens |
| 5,554,185 A | 9/1996 | Block et al. |
| 5,560,487 A | 10/1996 | Starr |
| 5,582,607 A | 12/1996 | Lackman |
| 5,607,442 A | 3/1997 | Fischell et al. |
| 5,620,456 A | 4/1997 | Sauer et al. |
| 5,668,425 A | 9/1997 | Marioni et al. |
| 5,695,515 A | 12/1997 | Orejola |
| 5,713,363 A | 2/1998 | Seward et al. |
| 5,713,860 A | 2/1998 | Kaplan et al. |
| 5,713,953 A | 2/1998 | Vallana et al. |
| 5,716,370 A | 2/1998 | Williamson et al. |
| 5,724,705 A | 3/1998 | Hauser et al. |
| 5,738,653 A | 4/1998 | Pinchuk et al. |
| 5,772,672 A | 6/1998 | Toy et al. |
| 5,814,097 A | 9/1998 | Sterman et al. |
| 5,814,098 A | 9/1998 | Hinnenkamp et al. |
| 5,823,342 A | 10/1998 | Caudillo et al. |
| 5,840,081 A | 11/1998 | Andersen et al. |
| 5,855,601 A | 1/1999 | Bessler et al. |
| 5,868,708 A | 2/1999 | Hart et al. |
| 5,891,195 A | 4/1999 | Klostermeyer et al. |
| 5,908,448 A | 6/1999 | Roberts et al. |
| 5,919,225 A | 7/1999 | Lau et al. |
| 5,921,926 A | 7/1999 | Rolland et al. |
| 5,921,993 A | 7/1999 | Yoon |
| 5,925,063 A | 7/1999 | Khosravi |
| 5,957,949 A | 9/1999 | Leonhardt et al. |
| 5,980,570 A | 11/1999 | Simpson |
| 5,984,959 A | 11/1999 | Robertson et al. |
| 6,010,511 A | 1/2000 | Murphy |
| 6,027,779 A | 2/2000 | Campbell et al. |
| 6,042,607 A | 3/2000 | Williamson, IV et al. |
| 6,051,014 A | 4/2000 | Jang |
| 6,053,922 A | 4/2000 | Krause et al. |
| 6,090,138 A | 7/2000 | Chasak et al. |
| 6,092,529 A | 7/2000 | Cox |
| 6,093,530 A | 7/2000 | McIlroy et al. |
| 6,102,944 A | 8/2000 | Huynh et al. |
| 6,102,945 A | 8/2000 | Campbell |
| 6,117,169 A | 9/2000 | Moe |
| 6,132,986 A | 10/2000 | Pathak et al. |
| 6,134,003 A | 10/2000 | Tearney et al. |
| 6,143,024 A | 11/2000 | Campbell et al. |
| 6,143,025 A | 11/2000 | Stobie et al. |
| 6,162,172 A | 12/2000 | Cosgrove et al. |
| 6,165,128 A * | 12/2000 | Cespedes et al. ............. 600/463 |
| 6,168,614 B1 | 1/2001 | Andersen et al. |
| 6,174,331 B1 | 1/2001 | Moe et al. |
| 6,182,664 B1 | 2/2001 | Cosgrove |
| 6,197,053 B1 | 3/2001 | Cosgrove et al. |
| 6,199,696 B1 | 3/2001 | Lytle et al. |
| 6,206,918 B1 | 3/2001 | Campbell et al. |
| 6,210,338 B1 | 4/2001 | Afremov et al. |
| 6,217,610 B1 | 4/2001 | Carpentier et al. |
| 6,231,578 B1 | 5/2001 | Rajhansa |
| 6,231,602 B1 | 5/2001 | Carpentier et al. |
| 6,240,307 B1 | 5/2001 | Beatty et al. |
| 6,241,665 B1 | 6/2001 | Negus et al. |
| 6,241,765 B1 | 6/2001 | GBriffin et al. |
| 6,245,102 B1 | 6/2001 | Jayaraman |
| 6,270,526 B1 | 8/2001 | Cox |
| 6,283,995 B1 | 9/2001 | Moe et al. |
| 6,287,339 B1 | 9/2001 | Vazquez et al. |
| 6,296,660 B1 | 10/2001 | Roberts et al. |
| 6,299,637 B1 | 10/2001 | Shaolian et al. |
| 6,299,638 B1 | 10/2001 | Sauter |
| 6,322,526 B1 | 11/2001 | Rosenman et al. |
| 6,338,740 B1 | 1/2002 | Carpentier |
| 6,342,070 B1 | 1/2002 | Nguyen-Thien-Nhon |
| 6,348,068 B1 | 2/2002 | Campbell et al. |
| 6,350,281 B1 | 2/2002 | Rhee |
| 6,350,732 B1 | 2/2002 | Moore et al. |
| 6,364,905 B1 | 4/2002 | Simpson et al. |
| 6,371,983 B1 | 4/2002 | Lane |
| 6,383,147 B1 | 5/2002 | Stobie |
| 6,391,054 B2 | 5/2002 | Carpentier et al. |
| 6,402,780 B2 | 6/2002 | Williamson, IV et al. |
| 6,405,084 B2 | 6/2002 | Plicchi et al. |
| 6,409,758 B2 | 6/2002 | Stobie et al. |
| 6,425,916 B1 | 7/2002 | Garrison et al. |
| 6,453,062 B1 | 9/2002 | MacNutt et al. |
| 6,454,799 B1 | 9/2002 | Schreck |
| 6,458,155 B1 | 10/2002 | Van Nguyen et al. |
| 6,461,382 B1 | 10/2002 | Cao |
| 6,475,239 B1 | 11/2002 | Campbell et al. |
| 6,479,079 B1 | 11/2002 | Pathak et al. |
| 6,482,228 B1 | 11/2002 | Norred |
| 6,485,512 B1 | 11/2002 | Cheng |
| 6,493,585 B2 | 12/2002 | Plicchi et al. |
| 6,522,913 B2 | 2/2003 | Swanson et al. |
| 6,530,952 B2 | 3/2003 | Vesely |
| 6,544,279 B1 | 4/2003 | Hopkins et al. |
| 6,546,272 B1 | 4/2003 | MacKinnon et al. |
| 6,558,418 B2 | 5/2003 | Carpentier et al. |
| 6,564,799 B2 | 5/2003 | Fukunaga et al. |
| 6,565,602 B2 | 5/2003 | Rolando et al. |
| 6,569,196 B1 | 5/2003 | Vesely |
| 6,572,642 B2 | 6/2003 | Rinaldi et al. |
| 6,582,462 B1 | 6/2003 | Andersen et al. |
| 6,585,632 B2 | 7/2003 | Vallana et al. |
| 6,585,766 B1 | 7/2003 | Huynh et al. |
| 6,596,471 B2 | 7/2003 | Pathak et al. |
| 6,602,288 B1 | 8/2003 | Cosgrove et al. |
| 6,607,502 B1 | 8/2003 | Maguire et al. |
| 6,613,085 B1 | 9/2003 | Anderson et al. |
| 6,616,690 B2 | 9/2003 | Rolando et al. |
| 6,635,085 B1 | 10/2003 | Caffey et al. |
| 6,638,303 B1 | 10/2003 | Campbell |

(56) References Cited

U.S. PATENT DOCUMENTS

| | | |
|---|---|---|
| 6,652,578 B2 | 11/2003 | Bailey et al. |
| 6,663,667 B2 | 12/2003 | Dehdashtian et al. |
| 6,673,109 B2 | 1/2004 | Cox |
| 6,679,871 B2 | 1/2004 | Hahnen |
| 6,682,543 B2 | 1/2004 | Barbut et al. |
| 6,682,558 B2 | 1/2004 | Tu et al. |
| 6,682,559 B2 | 1/2004 | Myers et al. |
| 6,689,149 B2 | 2/2004 | Maahs |
| 6,692,512 B2 | 2/2004 | Jang |
| 6,706,033 B1 | 3/2004 | Martinez et al. |
| 6,719,787 B2 | 4/2004 | Cox |
| 6,719,788 B2 | 4/2004 | Cox |
| 6,719,789 B2 | 4/2004 | Cox |
| 6,723,122 B2 | 4/2004 | Yang et al. |
| 6,730,118 B2 | 5/2004 | Spenser et al. |
| 6,733,513 B2 | 5/2004 | Boyle et al. |
| 6,733,525 B2 | 5/2004 | Yang et al. |
| 6,736,845 B2 | 5/2004 | Marquez et al. |
| 6,736,846 B2 | 5/2004 | Cox |
| 6,751,492 B2 | 6/2004 | Ben-Haim |
| 6,767,362 B2 | 7/2004 | Schreck |
| 6,770,083 B2 | 8/2004 | Seguin |
| 6,783,988 B1 | 8/2004 | Dinh et al. |
| 6,790,219 B1 | 9/2004 | Murphy |
| 6,796,972 B1 | 9/2004 | Sinofsky et al. |
| 6,797,000 B2 | 9/2004 | Simpson et al. |
| 6,805,710 B2 | 10/2004 | Bolling et al. |
| 6,821,279 B2 | 11/2004 | Di Emidio |
| 6,821,297 B2 | 11/2004 | Snyders |
| 6,846,324 B2 | 1/2005 | Stobie |
| 6,849,088 B2 | 2/2005 | Dehdashtian et al. |
| 6,858,039 B2 | 2/2005 | McCarthy |
| 6,869,431 B2 | 3/2005 | Maguire et al. |
| 6,875,231 B2 | 4/2005 | Anduiza et al. |
| 6,878,168 B2 | 4/2005 | Carpentier et al. |
| 6,879,851 B2 | 4/2005 | McNamara et al. |
| 6,893,460 B2 | 5/2005 | Spenser et al. |
| 6,896,698 B2 | 5/2005 | Rolando et al. |
| 6,898,168 B2 | 5/2005 | Kimura et al. |
| 6,908,481 B2 | 6/2005 | Cribier |
| 6,939,365 B1 | 9/2005 | Fogarty et al. |
| 6,942,680 B2 | 9/2005 | Grayzel et al. |
| 6,945,997 B2 | 9/2005 | Huynh et al. |
| 6,951,571 B1 | 10/2005 | Srivastava |
| 6,962,605 B2 | 11/2005 | Cosgrove et al. |
| 6,986,775 B2 | 1/2006 | Morales et al. |
| 6,988,881 B2 | 1/2006 | Motsenbocker et al. |
| 6,989,028 B2 | 1/2006 | Lashinski et al. |
| 7,004,176 B2 | 2/2006 | Lau |
| 7,007,396 B2 | 3/2006 | Rudko et al. |
| 7,011,669 B2 | 3/2006 | Kimblad |
| 7,011,681 B2 | 3/2006 | Vesely |
| 7,011,682 B2 | 3/2006 | Lashinski et al. |
| 7,014,648 B2 | 3/2006 | Ambrisco et al. |
| 7,018,406 B2 | 3/2006 | Seguin et al. |
| 7,060,092 B2 | 6/2006 | Kuribayashi et al. |
| 7,101,396 B2 | 9/2006 | Artof et al. |
| 7,252,682 B2 | 8/2007 | Seguin |
| 7,320,704 B2 * | 1/2008 | Lashinski et al. ............ 623/2.11 |
| 7,374,571 B2 | 5/2008 | Pease et al. |
| 7,381,219 B2 | 6/2008 | Salahieh et al. |
| 7,577,471 B2 | 8/2009 | Camus et al. |
| 7,616,987 B2 | 11/2009 | Premachandran et al. |
| 7,658,196 B2 | 2/2010 | Ferreri et al. |
| 8,057,396 B2 | 11/2011 | Forster et al. |
| 2001/0016758 A1 | 8/2001 | Plicchi et al. |
| 2001/0018600 A1 | 8/2001 | Plicchi et al. |
| 2001/0039450 A1 | 11/2001 | Pavcnik et al. |
| 2001/0049541 A1 | 12/2001 | Plicchi et al. |
| 2002/0010489 A1 | 1/2002 | Grayzel et al. |
| 2002/0032482 A1 | 3/2002 | Cox |
| 2002/0038128 A1 | 3/2002 | Turovkiy et al. |
| 2002/0042651 A1 | 4/2002 | Liddicoat et al. |
| 2002/0052647 A1 | 5/2002 | Rolando et al. |
| 2002/0055775 A1 | 5/2002 | Carpentier et al. |
| 2002/0058994 A1 | 5/2002 | Hill et al. |
| 2002/0072793 A1 | 6/2002 | Rolando et al. |
| 2002/0095173 A1 | 7/2002 | Mazzocchi et al. |
| 2002/0099441 A1 | 7/2002 | Dehdashtian |
| 2002/0117264 A1 | 8/2002 | Rinaldi et al. |
| 2002/0133226 A1 | 9/2002 | Marquez et al. |
| 2002/0138138 A1 | 9/2002 | Yang |
| 2002/0161431 A1 | 10/2002 | Stobie et al. |
| 2002/0163104 A1 | 11/2002 | Motsenbocker et al. |
| 2002/0183766 A1 | 12/2002 | Seguin |
| 2002/0183831 A1 | 12/2002 | Rolando et al. |
| 2003/0009076 A1 | 1/2003 | Vallana et al. |
| 2003/0023262 A1 | 1/2003 | Welch |
| 2003/0027332 A1 | 2/2003 | Lafrance et al. |
| 2003/0033002 A1 | 2/2003 | Dehdashtian et al. |
| 2003/0036795 A1 | 2/2003 | Andersen et al. |
| 2003/0050694 A1 | 3/2003 | Yang et al. |
| 2003/0055495 A1 | 3/2003 | Pease et al. |
| 2003/0065356 A1 | 4/2003 | Tsugita et al. |
| 2003/0092977 A1 | 5/2003 | Sahatjian |
| 2003/0105509 A1 | 6/2003 | Jang et al. |
| 2003/0114913 A1 | 6/2003 | Spenser et al. |
| 2003/0114917 A1 | 6/2003 | Holloway et al. |
| 2003/0130721 A1 | 7/2003 | Martin et al. |
| 2003/0153943 A1 | 8/2003 | Michael et al. |
| 2003/0153946 A1 | 8/2003 | Kimblad |
| 2003/0195613 A1 | 10/2003 | Curcio et al. |
| 2003/0212433 A1 | 11/2003 | Ambrisco et al. |
| 2004/0010209 A1 | 1/2004 | Sirokman |
| 2004/0030382 A1 | 2/2004 | St. Goar et al. |
| 2004/0034380 A1 | 2/2004 | Woolfson et al. |
| 2004/0049266 A1 | 3/2004 | Anduiza et al. |
| 2004/0078074 A1 | 4/2004 | Anderson et al. |
| 2004/0092858 A1 | 5/2004 | Wilson et al. |
| 2004/0092989 A1 | 5/2004 | Wilson et al. |
| 2004/0093060 A1 | 5/2004 | Seguin et al. |
| 2004/0093080 A1 | 5/2004 | Helmus et al. |
| 2004/0127979 A1 | 7/2004 | Wilson et al. |
| 2004/0127982 A1 * | 7/2004 | Machold et al. ............ 623/2.36 |
| 2004/0148017 A1 | 7/2004 | Stobie |
| 2004/0148018 A1 | 7/2004 | Carpentier et al. |
| 2004/0153140 A1 | 8/2004 | Rolando et al. |
| 2004/0158276 A1 | 8/2004 | Barbut et al. |
| 2004/0172124 A1 | 9/2004 | Vallana et al. |
| 2004/0186563 A1 | 9/2004 | Lobbi |
| 2004/0193259 A1 | 9/2004 | Gabbay |
| 2004/0210304 A1 | 10/2004 | Seguin et al. |
| 2004/0225352 A1 | 11/2004 | Osborne et al. |
| 2004/0249433 A1 | 12/2004 | Freitag |
| 2005/0027337 A1 | 2/2005 | Rudko et al. |
| 2005/0033398 A1 | 2/2005 | Seguin |
| 2005/0038497 A1 | 2/2005 | Neuendorf et al. |
| 2005/0043792 A1 | 2/2005 | Solem et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075725 A1 | 4/2005 | Rowe |
| 2005/0085903 A1 * | 4/2005 | Lau ............................ 623/2.11 |
| 2005/0090846 A1 | 4/2005 | Pedersen et al. |
| 2005/0090888 A1 | 4/2005 | Hines et al. |
| 2005/0096740 A1 | 5/2005 | Langberg et al. |
| 2005/0102020 A1 | 5/2005 | Grayzel et al. |
| 2005/0113686 A1 | 5/2005 | Peckham |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |

(56) References Cited

U.S. PATENT DOCUMENTS

| | | |
|---|---|---|
| 2005/0228485 A1 | 10/2005 | Rolando et al. |
| 2005/0267493 A1 | 12/2005 | Schreck et al. |
| 2005/0277959 A1 | 12/2005 | Cosgrove et al. |
| 2005/0283232 A1 | 12/2005 | Gabbay |
| 2006/0015133 A1 | 1/2006 | Grayzel et al. |
| 2006/0015179 A1 | 1/2006 | Bulman-Fleming et al. |
| 2006/0020332 A1 | 1/2006 | Lashinski et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0058871 A1 | 3/2006 | Zakay et al. |
| 2006/0095052 A1 | 5/2006 | Chambers |
| 2006/0122633 A1 | 6/2006 | To et al. |
| 2006/0173537 A1 | 8/2006 | Yang et al. |
| 2006/0217764 A1 | 9/2006 | Abbott et al. |
| 2006/0235511 A1 | 10/2006 | Osborne |
| 2006/0259137 A1* | 11/2006 | Artof et al. ............ 623/2.18 |
| 2007/0015964 A1 | 1/2007 | Eversull et al. |
| 2007/0016286 A1 | 1/2007 | Herrmann et al. |
| 2007/0083217 A1 | 4/2007 | Eversull et al. |
| 2007/0088431 A1 | 4/2007 | Bourang et al. |
| 2007/0149878 A1 | 6/2007 | Hankins |
| 2007/0185571 A1* | 8/2007 | Kapadia et al. ......... 623/2.11 |
| 2007/0219451 A1 | 9/2007 | Kula et al. |
| 2008/0009746 A1 | 1/2008 | Forster et al. |
| 2008/0140172 A1 | 6/2008 | Carpenter et al. |
| 2008/0255449 A1 | 10/2008 | Warnking et al. |
| 2009/0005674 A1 | 1/2009 | Saadat et al. |
| 2009/0143686 A1 | 6/2009 | Onimura et al. |
| 2009/0171157 A1 | 7/2009 | Diederich et al. |
| 2009/0287183 A1 | 11/2009 | Bishop et al. |
| 2009/0323076 A1 | 12/2009 | Li et al. |
| 2010/0094209 A1 | 4/2010 | Drasler et al. |
| 2010/0168836 A1 | 7/2010 | Kassab |
| 2010/0179424 A1 | 7/2010 | Warnking et al. |
| 2010/0217119 A1 | 8/2010 | Forster et al. |
| 2012/0051472 A1 | 3/2012 | Akahori |
| 2012/0051474 A1 | 3/2012 | Yu et al. |
| 2012/0064623 A1 | 3/2012 | Zijlstra et al. |
| 2012/0064624 A1 | 3/2012 | Lu et al. |

FOREIGN PATENT DOCUMENTS

| | | |
|---|---|---|
| WO | WO 01/76510 A2 | 10/2001 |
| WO | WO 03/003949 A2 | 1/2003 |
| WO | WO 03/047468 A1 | 6/2003 |
| WO | WO 03/105670 A2 | 12/2003 |
| WO | WO 2005009285 A2 | 2/2005 |
| WO | WO 2005/076973 A2 | 8/2005 |
| WO | WO 2005/087140 A1 | 9/2005 |

OTHER PUBLICATIONS

U.S. Appl. No. 11/066,126—Office Action, Apr. 3, 2009.
U.S. Appl. No. 11/066,126—Office Action, Dec. 22, 2009.
U.S. Appl. No. 11/066,124—Office Action, Mar. 7, 2007.
U.S. Appl. No. 11/066,124—Office Action, Mar. 7, 2008.
U.S. Appl. No. 11/066,124—Office Action, Oct. 2, 2008.
U.S. Appl. No. 11/066,124—Office Action, Jun. 9, 2009.
U.S. Appl. No. 11/067,330—Office Action, Apr. 16, 2007.
U.S. Appl. No. 11/067,330—Office Action, Jun. 11, 2008.
U.S. Appl. No. 11/067,330—Office Action, Jun. 10, 2009.
U.S. Appl. No. 11/364,715—Office Action, Dec. 11, 2006.
U.S. Appl. No. 11/364,715—Office Action, Oct. 18, 2007.
U.S. Appl. No. 11/364,715—Office Action, Jan. 12, 2009.
CN, Ser. No. 200580012735.5—Office Action, Jan. 9, 2009.
CN, Ser. No. 200580012735.5—Office Action, Jul. 10, 2009.
EP, Ser. No. 05723873.5—ESR, Nov. 3, 2009.
WO, Ser. No. WO2007/101159—ISR, Apr. 24, 2008.
WO, Ser. No. WO2007/101160—ISR, Dec. 11, 2007.
WO, Ser. No. WO2007/149905—ISR, Aug. 29, 2008.
WO, Ser. No. WO2007/149841—ISR, Jul. 30, 2008.
WO, Ser. No. WO2007/149933—ISR, Aug. 15, 2008.
WO, Ser. No. WO2007/149910—ISR, Jan. 28, 2008.
WO, Ser. No. WO2008/030946—ISR, Jan. 11, 2008.
PCT ISR PCTUS2011056240, mailed Jan. 31, 2012.
PCT WO PCTUS2011056240, mailed Jan. 31, 2012.
PCT ISR PCT2011056243, mailed Feb. 14, 2012.
PCT WO PCT2011056243, mailed Feb. 14, 2012.
PCT ISR PCTUS2011067542, mailed Jun. 20, 2012.
PCT WO PCTUS2011067542, mailed Jun. 20, 2012.

* cited by examiner

METHODS OF ASSESSING INNER SURFACES OF BODY LUMENS OR ORGANS

CROSS REFERENCES TO RELATED APPLICATIONS

This application relates to U.S. patent application Ser. No. 11/066,126, entitled "Prosthetic Heart Valves, Scaffolding Structures, and Methods for Implantation of Same," filed Feb. 25, 2005, which application is hereby incorporated by reference in its entirety. The foregoing application claims the benefit of U.S. Provisional Application Ser. No. 60/548,731, entitled "Foldable Stent for Minimally Invasive Surgery," filed Feb. 27, 2004, and U.S. Provisional Application Ser. No. 60/559,199, entitled "Method and Multiple Balloon for Percutaneous Aortic Valve Implantation," filed Apr. 1, 2004, each of which applications is hereby incorporated by reference in its entirety.

FIELD OF THE INVENTION

The present invention relates generally to medical devices and methods. More particularly, the present invention relates to methods and devices for assessing the shape, size, topography, compliance, and other aspects of cardiac valves and surrounding tissue. The devices and methods are particularly adapted for use during minimally invasive surgical interventions, but may also find application during surgical replacement on a stopped heart, less invasive surgical procedures on a beating heart, and other percutaneous procedures.

BACKGROUND OF THE INVENTION

Minimally invasive surgery provides several advantages over conventional surgical procedures, including reduced recovery time, reduced surgically-induced trauma, and reduced post-surgical pain. Moreover, the expertise of surgeons performing minimally invasive surgery has increased significantly since the introduction of such techniques in the 1980s. As a result, substantial focus has been paid over the past twenty years to devices and methods for facilitating and improving minimally invasive surgical procedures.

One area in which there remains a need for substantial improvement is pre-surgical assessment of treatment locations intended to be subjected to a minimally invasive surgical procedure. For example, when a surgical procedure is to be performed at a treatment location within the body of a patient, it would frequently be beneficial for the surgeon to have prior knowledge of the shape, size, topography, compliance, and other physical properties of the treatment location. This information would be particularly useful in relation to minimally invasive surgical procedures in which prosthetic devices are implanted within a body lumen or within a hollow portion of an organ located within the body of the patient. Such information could then be used to select the size and/or shape of the prosthetic device to more closely match the size, shape, and topography of the treatment location.

Several devices and methods for assessing particular anatomical treatment locations are known to those skilled in the art. For example, ultrasonic imaging devices have been used to assess certain anatomical structures. See, for example, U.S. Pat. No. 5,240,004, which describes, intravascular, ultrasonic imaging catheters that are used for ultrasonic imaging the walls of potentially diseased vessels having relatively small diameters. Similarly, U.S. Pat. No. 5,713,363 describes an ultrasonic and interventional catheter which provides imaging and hemodynamics, blood pressure and flow capabilities.

Still further, U.S. Pat. No. 6,751,492 describes the use of ultrasonic position sensors to map portions of the heart. Alternatively, devices that transmit and receive electronic signals have been used to assess certain anatomical structures. See, for example, U.S. Published Application No. 2003/0092977 A1, which describes a catheter-based system for diagnosing lesions in tissue through use of piezoelectric elements mounted on the distal end of the catheter. Other alternative devices and methods are described in U.S. Pat. No. 6,241,665, which describes a percutaneous mapping system that includes a mapping wire having imaging markers disposed thereon. The markers may be radiopaque, ultrasonically sensible, or electromagnetically sensible. Each of the foregoing patents and publications is hereby incorporated by reference in its entirety. Many other devices for performing mapping and/or assessing functions are known to those skilled in the art.

A particular portion of the anatomy for which complete and accurate physical assessment would be beneficial, and for which no such assessment has been provided by the devices and methods of the known prior art, are the coronary valves. Diseases and other disorders of heart valves affect the proper flow of blood from the heart. Two categories of heart valve disease are stenosis and incompetence. Stenosis refers to a failure of the valve to open fully, due to stiffened valve tissue. Incompetence refers to valves that cause inefficient blood circulation, permitting backflow of blood in the heart.

Medication may be used to treat some heart valve disorders, but many cases require replacement of the native valve with a prosthetic heart valve. In such cases, a thorough assessment of the shape, size, topography, compliance, and other physical properties of the native valve annulus would be extremely beneficial. Prosthetic heart valves can be used to replace any of the native heart valves (aortic, mitral, tricuspid or pulmonary), although repair or replacement of the aortic or mitral valves is most common because they reside in the left side of the heart where pressures are the greatest. Two primary types of prosthetic heart valves are commonly used, mechanical heart valves and prosthetic tissue heart valves.

The caged ball design is one of the early mechanical heart valves. The caged ball design uses a small ball that is held in place by a welded metal cage. In the mid-1960s, another prosthetic valve was designed that used a tilting disc to better mimic the natural patterns of blood flow. The tilting-disc valves had a polymer disc held in place by two welded struts. The bileaflet valve was introduced in the late 1970s. It included two semicircular leaflets that pivot on hinges. The leaflets swing open completely, parallel to the direction of the blood flow. They do not close completely, which allows some backflow.

The main advantages of mechanical valves are their high durability. Mechanical heart valves are placed in young patients because they typically last for the lifetime of the patient. The main problem with all mechanical valves is the increased risk of blood clotting.

Prosthetic tissue valves include human tissue valves and animal tissue valves. Both types are often referred to as bioprosthetic valves. The design of bioprosthetic valves are closer to the design of the natural valve. Bioprosthetic valves do not require long-term anticoagulants, have better hemodynamics, do not cause damage to blood cells, and do not suffer from many of the structural problems experienced by the mechanical heart valves.

Human tissue valves include homografts, which are valves that are transplanted from another human being, and autografts, which are valves that are transplanted from one position to another within the same person.

Animal tissue valves are most often heart tissues recovered from animals. The recovered tissues are typically stiffened by a tanning solution, most often glutaraldehyde. The most commonly used animal tissues are porcine, bovine, and equine pericardial tissue.

The animal tissue valves are typically stented valves. Stentless valves are made by removing the entire aortic root and adjacent aorta as a block, usually from a pig. The coronary arteries are tied off, and the entire section is trimmed and then implanted into the patient.

A conventional heart valve replacement surgery involves accessing the heart in the patent's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. After the heart has been arrested the aorta is cut open to allow access to the diseased valve for replacement. Such open heart surgery is particularly invasive and involves a lengthy and difficult recovery period.

Less invasive approaches to valve replacement have been proposed. The percutaneous implantation of a prosthetic valve is a preferred procedure because the operation is performed under local anesthesia, does not require cardiopulmonary bypass, and is less traumatic. Current attempts to provide such a device generally involve stent-like structures, which are very similar to those used in vascular stent procedures with the exception of being larger diameter as required for the aortic anatomy, as well as having leaflets attached to provide one way blood flow. These stent structures are radially contracted for delivery to the intended site, and then expanded/deployed to achieve a tubular structure in the annulus. The stent structure needs to provide two primary functions. First, the structure needs to provide adequate radial stiffness when in the expanded state. Radial stiffness is required to maintain the cylindrical shape of the structure, which assures the leaflets coapt properly. Proper leaflet coaption assures the edges of the leaflets mate properly, which is necessary for proper sealing without leaks. Radial stiffness also assures that there will be no paravalvular leakage, which is leaking between the valve and aorta interface, rather than through the leaflets. An additional need for radial stiffness is to provide sufficient interaction between the valve and native aortic wall that there will be no valve migration as the valve closes and holds full body blood pressure. This is a requirement that other vascular devices are not subjected to. The second primary function of the stent structure is the ability to be crimped to a reduced size for implantation.

Prior devices have utilized traditional stenting designs which are produced from tubing or wire wound structures. Although this type of design can provide for crimpability, it provides little radial stiffness. These devices are subject to "radial recoil" in that when the device is deployed, typically with balloon expansion, the final deployed diameter is smaller than the diameter the balloon and stent structure were expanded to. The recoil is due in part because of the stiffness mismatches between the device and the anatomical environment in which it is placed. These devices also commonly cause crushing, tearing, or other deformation to the valve leaflets during the contraction and expansion procedures. Other stenting designs have included spirally wound metallic sheets. This type of design provides high radial stiffness, yet crimping results in large material strains that can cause stress fractures and extremely large amounts of stored energy in the constrained state. Replacement heart valves are expected to survive for many years when implanted. A heart valve sees approximately 600,000,000 cycles over the course of 15 years. High stress states during crimping can reduce the fatigue life of the device. Still other devices have included tubing, wire wound structures, or spirally wound sheets formed of nitinol or other superelastic or shape memory material. These devices suffer from some of the same deficiencies as those described above.

A number of improved prosthetic heart valves and scaffolding structures are described in co-pending U.S. patent application Ser. No. 11/066,126, entitled "Prosthetic Heart Valves, Scaffolding Structures, and Methods for Implantation of Same," filed Feb. 25, 2005, ("the '126 application") which application is hereby incorporated by reference in its entirety. Several of the prosthetic heart valves described in the '126 application include a support member having a valvular body attached, the support member preferably comprising a structure having a plurality of panels separated by foldable junctions. The '126 application also describes several delivery mechanisms adapted to deliver the described prosthetic heart valve.

Accordingly, a need exists for devices and methods that provide assessment information concerning the size, shape, topography, compliance, and other physical properties of the native cardiac valves in order to facilitate proper selection and placement of prosthetic heart valves.

SUMMARY OF THE INVENTION

The present invention provides methods and devices for assessing the shape, size, topography, compliance, and other physical properties of a vessel lumen or a hollow portion of another organ located within a patient. The methods and devices may find use in the coronary vasculature, the peripheral vasculature, the abdominal vasculature, and in other ducts such as the biliary duct, the fallopian tubes, and similar lumen structures within the body of a patient. The methods and devices may also find use in the heart, lungs, kidneys, or other organs within the body of a patient. Moreover, although particularly adapted for use in vessels and organs found in the human body, the apparatus and methods may also find application in the treatment of animals.

However, the primary use of the methods and devices described herein is in the assessment of the size, shape, topography, compliance, spatial orientation, and other physical properties of the native heart valves. Such assessments are useful to facilitate proper sizing, selection, and implantation of prosthetic heart valves into the native valve space. Proper selection and sizing ensures that the prosthetic heart valve that is delivered during the implantation procedure will be of a size and shape that fits within the native valve space, including accommodations for any defects or deformities that are detected by the assessment process. Proper selection and sizing also ensures that the prosthetic valve, once fully expanded, will properly seal against the aortic wall to prevent leakage, and to prevent migration of the prosthetic valve.

The methods and devices described herein are suitable for use in facilitating the selection and sizing of prosthetic heart valves of all types, independent of the design, implantation mechanism, deployment technique, or any other aspect of the prosthetic valve. In many cases, particularly in the case of a prosthetic valve that is expandable from a delivery state to a deployed state, the assessment of the native valve space is of very great importance. For example, it is important to know the diameter of the native valve space when the valve space has been placed under the expansive load that is produced by the prosthetic valve. If the valve does not fit properly, it may migrate, leak, or resist deployment altogether.

The methods include use of an assessment member that is preferably located at or near the distal end of a catheter or other similar device. The assessment member is introduced to a treatment location within the patient, preferably the native cardiac valve, where the assessment member is activated or otherwise put into use to perform an assessment of one or more physical parameters of the treatment location, to collect the assessment information, and to provide the assessment information to the clinician. Typical assessment information includes the size (e.g., diameter, circumference, area, volume, etc.) of the valve space, the shape (e.g., round, spherical, irregular, etc.) of the lumen or hollow portion of the organ, the topography (e.g., locations, sizes, and shapes of any irregular features) of the lumen or hollow portion of the organ, the compliance (e.g., the degree or amount of expansion and the amount of resistance to expansion) of the lumen or hollow portion of the organ, the nature of any regular or irregular features (e.g., thrombosis, calcification, healthy tissue, fibrosa), the spatial orientation (e.g., absolute location relative to a fixed reference point, or directional orientation) of a point or other portion of the treatment location, and other physical properties. Access to the treatment location is obtained by any conventional method, such as by general surgical techniques, less invasive surgical techniques, or percutaneously. A preferred method of accessing the treatment location is transluminally, preferably by well-known techniques for accessing the vasculature from a location such as the femoral artery. The catheter is preferably adapted to engage and track over a guidewire that has been previously inserted and routed to the treatment site.

Any suitable assessment mechanism or technology may be used, including all of the mechanisms known to those of ordinary skill in the art that have been used for mapping, assessing, or otherwise determining anatomical structures. Several examples of such mechanisms are described above in the Background section. Examples of some of these assessment mechanisms include ultrasonic imaging devices (intra cardiac echo, 3D ultrasound), electrode-based mapping or imaging systems, electronic topographical mapping devices, other electronic signal transmitting and receiving systems (e.g., piezoelectric and others), fluoroscopic imaging of radiopaque markers, sizing balloons, and other mechanisms. In addition, any known method for three-dimensional external imaging of internal features may be used, such as magnetic resonance imaging (MRI), computed tomography (CT scan), external scanning of sonomicrometry crystals, external scanning of other contrast media, and all other similar methods known to those of skill in the art.

In several embodiments, the assessment mechanism includes an expandable member that is attached to the catheter shaft at or near its distal end. The expandable member may comprise an inflatable balloon, a structure containing a plurality of interconnected metallic or polymeric springs or struts, an expandable "wisk"—like structure, or other suitable expandable member. In the case of an inflatable balloon, the expandable member is operatively connected to a source of inflation medium that is accessible at or near the proximal end of the catheter. The expandable member has at least two states, an unexpanded state and an expanded state. The unexpanded state generally corresponds with delivery of the assessment mechanism through the patient's vasculature. The expanded state generally corresponds with the assessment process. The expandable member is adapted to provide assessment information to the user when the expandable member is engaged with a treatment location within the body of a patient.

Turning to several exemplary measurement devices and methods, in one aspect of the invention, a catheter-based system includes a transluminal imaging device contained partially or entirely within an expandable structure attached at or near the distal end of the catheter. The imaging device may comprise any suitable acoustic or other device used for imaging processes, such as intravascular ultrasonic imaging processes. In the preferred embodiment, the imaging device is an ultrasonic imaging probe that is configured to transmit and receive ultrasonic signals at a desired frequency or at a plurality of desired frequencies. The received signals are then used to calculate measurement information, which measurement information is then captured for later use or displayed to the clinician through a suitable display.

In the preferred embodiments, the expandable structure is a balloon member. The balloon member is connected to an inflation lumen that runs between the proximal and distal ends of the catheter, and that is selectively attached to a source of inflation medium at or near the proximal end of the catheter. The balloon member is thereby selectively expandable while the imaging device is located either partially or entirely within the interior of the balloon. The imaging device is adapted to be advanced, retracted, and rotated within the balloon, thereby providing for imaging in a plurality of planes and providing the ability to produce three-dimensional images of the treatment site.

In optional embodiments, the expandable structure is filled with a medium that enhances the imaging process. For example, the medium may comprise a material that increases the transmission capabilities of the ultrasonic waves or other imaging energy, or that reduces the amount of scattering of the imaging energy that would otherwise occur without use of the imaging-enhancing medium. In still other optional embodiments, the expandable structure contains (e.g., has embedded or formed within) or is formed of a material that enhances the imaging process. In still other embodiments, the expandable structure includes a layer of or is coated with a material that enhances the imaging process. Other and further optional embodiments are also contemplated.

In use, the transluminal imaging device is first introduced to the target location within the patient, such as the native valve annulus. In the preferred embodiment, this is achieved by introducing the catheter through the patient's vasculature to the target location. Typically, the catheter tracks over a guidewire that has been previously installed in any suitable manner. The imaging device may be provided with a radiopaque or other suitable marker at or near its distal end in order to facilitate delivery of the imaging device to the target location by fluoroscopic visualization or other suitable means. Once the imaging device is properly located at the target location, the expandable structure is expanded by introducing an expansion medium through the catheter lumen. The expandable structure expands such that it engages and applies pressure to the internal walls of the target location, such as the valve annulus. The expandable structure also takes on the shape of the internal surface of the target location, including all contours or other topography. Once the expandable structure has been sufficiently expanded, the imaging device is activated. Where appropriate, the imaging device is advanced, retracted, and/or rotated to provide sufficient movement to allow a suitable image of the target location to be created, or to collect a desired amount of measurement information. The measurement information collected and/or the images created by the imaging device are then transmitted to a suitable user interface, where they are displayed to the clinician.

In another aspect of the present invention, a physical assessment member includes an expandable member attached to a catheter at or near the distal end thereof. A suitable inflation lumen is provided on the catheter to connect the expandable member to a source of inflation medium located at or near the proximal end of the catheter. In several preferred embodiments, the expandable member is a balloon having a suitable indexing means that is formed integrally with, attached to, or otherwise carried by the expandable member. The indexing means provides a mechanism for determining the size, shape, or other physical property of a target location, such as a vessel lumen or hollow portion of an organ within a patient. The physical assessment member is particularly adapted to determine the size, shape, topography, and physical properties of a native heart valve annulus.

For example, in a first embodiment, the indexing means includes a tapered distal end of the expandable member. The tapered distal end is provided with a plurality of radiopaque markers, each of which corresponds to a size (e.g., diameter, circumference) for the lumen or organ encountered by the distal end of the expandable member. The markers may be provided in a horizontal orientation, a vertical orientation, or other suitable orientation.

In an alternative embodiment, the indexing means includes a plurality of graduated steps formed on the distal end of the expandable member. The graduated steps each correspond to a size (e.g., diameter, circumference) for the lumen or organ encountered by the distal end of the expandable member. The expandable member is provided with one or more suitable radiopaque markers to provide position information. The expandable member may optionally also include an alignment mechanism that includes first and second radiopaque markers having a predetermined relative orientation.

In use, the physical assessment member is first introduced to the target location within the patient. In the preferred embodiment, this is achieved by introducing the catheter through the patient's vasculature to the target location. The catheter tracks over a guidewire that has been previously installed in any suitable manner. The expandable member carried on the catheter may be provided with a radiopaque or other suitable marker at or near its distal end in order to facilitate delivery of the physical assessment member to the target location by fluoroscopic visualization or other suitable means. Once the expandable member is properly located at the target location, the expandable member is expanded by introducing an expansion medium through the catheter lumen. The expandable member expands to a predetermined size such that the indexing means is able to engage the lumen or hollow portion of the organ, thereby providing an indicator of the size (e.g., diameter, circumference) of the lumen or hollow portion of the organ by proper visualization of the indexing means. In this way, the clinician is able to obtain precise measurements of the size of the lumen or hollow portion of the organ at the target location.

In still another aspect of the present invention, an electronic mapping member includes an expandable member attached to a catheter at or near the distal end thereof. A suitable inflation lumen is provided on the catheter to connect the expandable member to a source of inflation medium located at or near the proximal end of the catheter. In several preferred embodiments, the expandable member is a balloon having a suitable electronic mapping construction affixed to or embedded within the expandable member. The electronic mapping construction provides a mechanism for determining the size, shape, compliance, or other physical properties of a target location, such as a vessel lumen or hollow portion of an organ within a patient.

For example, in a first embodiment, the electronic mapping construction includes a plurality of conductors (e.g., conductive wires) extending generally longitudinally along the surface or embedded within the expandable member. The conductors are each spaced a known distance apart from one another. Preferably, each conductor is spaced apart from its adjacent conductor by the same distance around the circumference of the expandable member. The conductors are electrically connected to a source of electrical energy. When activated, the conductors form a plurality of circuits that generate an electrical signal with one another. For example, a first conductor carrying a given current or loaded with a given voltage will create an inductance, a capacitance, or other measurable electrical signal with respect to a second conductor located at a second position relative to the first conductor. These electrical interference properties are measurable, and are able to be converted into distance measurements or other physical measurements. As measurements are taken for each conductor relative to each other conductor, a mapping of the location and orientation of each of the conductors is created, thereby creating a topographic map of the target location.

In alternative embodiments, additional circuits of conductors are fixed to the surface or embedded within the expandable member. For example, in some embodiments, the additional circuits of conductors are aligned generally perpendicularly to the first sets of conductors. In other embodiments, still further circuits of electrical conductors are nested within other circuits. By proper orientation and selection of the plurality of circuits of conductors, a 3-dimensional electronic mapping is generated, providing size, shape, and other topographic information relating to the lumen or hollow portion of an organ within the patient.

In use, the electronic mapping member is first introduced to the target location within the patient. In the preferred embodiment, this is achieved by introducing the catheter through the patient's vasculature to the target location. The catheter tracks over a guidewire that has been previously installed in any suitable manner. The expandable member carried on the catheter may be provided with a radiopaque or other suitable marker at or near its distal end in order to facilitate delivery of the electronic mapping member to the target location by fluoroscopic visualization or other suitable means. Once the expandable member is properly located at the target location, the expandable member is expanded by introducing an expansion medium through the catheter lumen. The expandable member expands to occupy the vessel lumen or hollow portion of the organ and to engage the internal surfaces thereof. Once the expandable member is fully expanded, an electrical input is placed over the one or more circuits of electrical conductors, thereby generating one or more signals between the conductors. The signal information is collected by suitable measuring instrumentation or other mechanisms and is provided to a data processor coupled to a user interface to display the measurement information to the clinician.

Alternatively, the electronic mapping construction comprises a plurality of sensing electrodes that extend longitudinally along the surface or are embedded within the expandable member. The sensing electrodes may operate in any suitable manner that provides position-indicating information to facilitate a mapping process. The orientation of the electrodes on the expandable member may be varied to obtain suitable results.

In still another aspect of the present invention, a multi-function catheter is provided with one or more of an alignment mechanism, a conventional valvuloplasty balloon, and a sizing and compliance diagnostic balloon. The alignment mechanism is particularly adapted to engage a predetermined portion of the anatomy of a patient, such as the native valve leaflets of the aortic valve of the patient. The conventional valvuloplasty balloon is preferably of a structure and formed of a material adapted to engage the native valve leaflets of a heart valve to perform a valvuloplasty procedure. The sizing and compliance diagnostic balloon, on the other hand, is preferably of a structure and formed of a material adapted to perform the sizing and compliance determinations. A resistance strip or other suitable member to measure strain in the stretched balloon is attached to or formed integrally with the diagnostic balloon over a portion thereof, thereby providing a correlation between pressure of the diagnostic balloon and circumferential length. The circumferential length is then able to be measured based upon the strain experienced along the perimeter of the balloon, while the compliance is proportional to the pressure encountered by the balloon upon engagement with the internal walls of the lumen or hollow portion of the organ.

In use, the multi-function catheter is first introduced to the target location within the patient. In the preferred embodiment, the target location is the native aortic valve, and introduction is achieved by introducing the catheter through the patient's vasculature to the target location. The catheter tracks over a guidewire that has been previously installed in any suitable manner. The distal portion of the catheter may be provided with a radiopaque or other suitable marker at or near its distal end in order to facilitate delivery of the valvuloplasty balloon to the target location by fluoroscopic visualization or other suitable means. Once the distal portion of the catheter is properly located at the target location, the alignment mechanism is extended such that the alignment wires are expanded to lodge in the sinus behind the native valve leaflets. A valvuloplasty procedure is then performed using the valvuloplasty balloon, after which the valvuloplasty balloon is deflated. Then, the diagnostic balloon is inflated until the balloon engages the annulus of the aortic valve root, at which point a pressure measurement is taken and is used to calculate the correlated size of the valve annulus.

In a further aspect of the present invention, a valvuloplasty procedure is performed in association with the assessment of the native cardiac valve. In a first embodiment, the expandable member contained on the assessment device also functions as a valvuloplasty balloon. The expandable member is placed within the cardiac valve space, where it is expanded. Expansion of the expandable member causes the native valve to increase in size and forces the valve, which is typically in a diseased state in which it is stiff and decreased in diameter, to open more broadly. The valvuloplasty procedure may therefore be performed prior to the deployment of a prosthetic valve, but during a single interventional procedure. Alternatively, the valvuloplasty procedure may eliminate the need for deploying a prosthetic valve.

The measurement and diagnostic processes performed by any of the foregoing devices and methods may be used to facilitate any suitable medical diagnosis, treatment, or other therapeutic processes. One particular treatment that is facilitated by the foregoing devices and methods is the repair and/or replacement of coronary vales, particular aortic valve replacement using a prosthetic valve. Many prosthetic heart valves, delivery devices, and delivery methods are described in the '126 application and others listed elsewhere herein. In those procedures, proper measurement and assessment of the aortic valve root may be very helpful in selecting and then delivering a properly-sized and properly-shaped prosthetic valve.

Other aspects, features, and functions of the inventions described herein will become apparent by reference to the drawings and the detailed description of the preferred embodiments set forth below.

DETAILED DESCRIPTION OF THE PREFERRED EMBODIMENTS

The present invention is directed to methods and devices for assessing the shape, size, topography, contours, and other aspects of anatomical vessels and organs using minimally invasive surgical techniques. As summarized above, the devices are typically catheter-based devices having one or more assessment mechanisms associated with the distal portion of the catheter. Such devices are suitable for use during less invasive and minimally invasive surgical procedures. However, it should be understood that the devices and methods described herein are also suitable for use during surgical procedures that are more invasive than the preferred minimally invasive techniques described herein.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present inventions.

Figure 1:
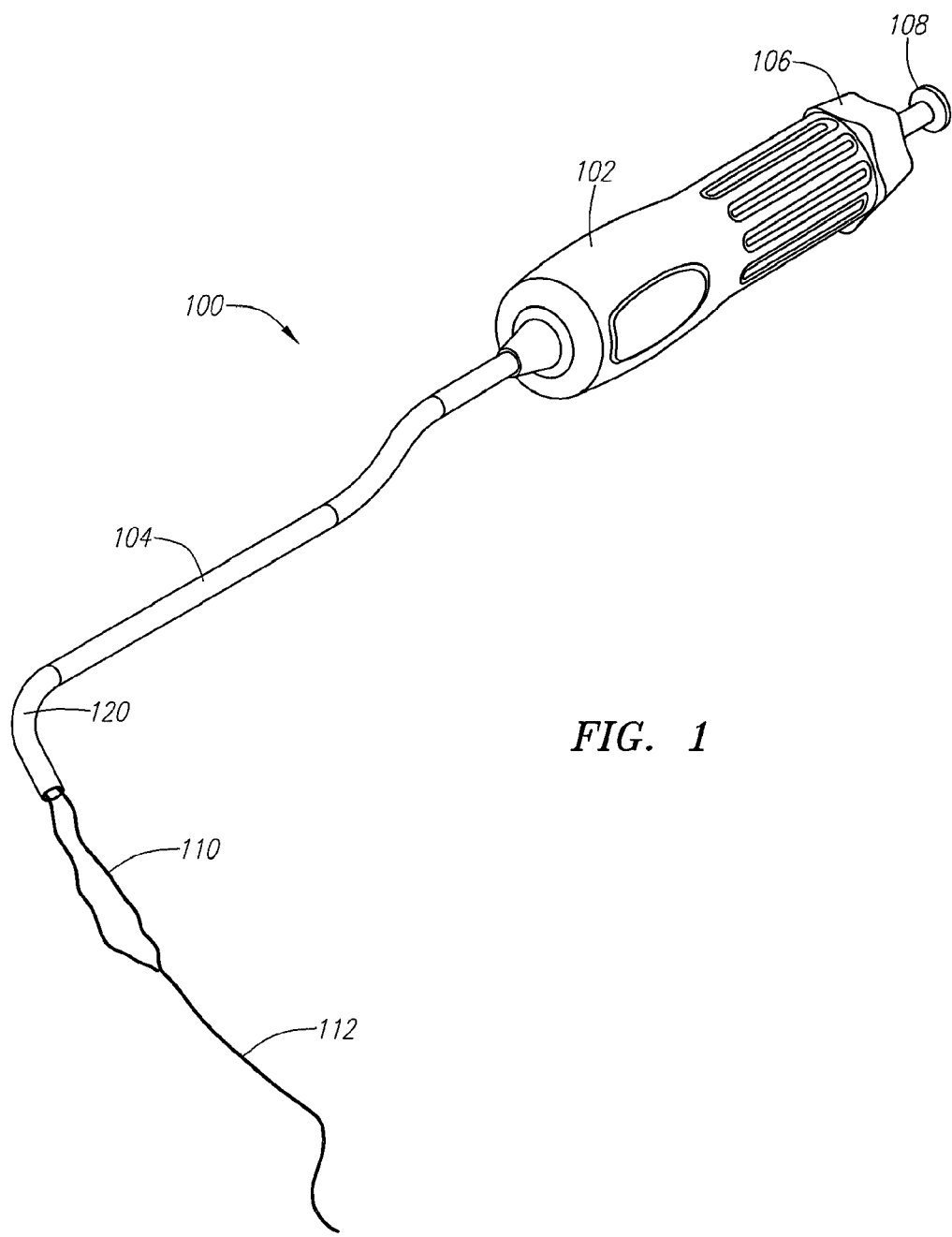
FIG. 1 is a perspective view of a catheter in accordance with several of the embodiments of the present invention.

Turning to the drawings, FIG. 1 shows a catheter 100 suitable for use with each of the assessment mechanisms described herein. The catheter 100 includes a handle 102 attached to the proximal end of an elongated catheter shaft 104. The size and shape of the handle 102 may vary, as may the features and functionality provided by the handle 102. In the illustrated embodiment, the handle 102 includes a knob 106 rotatably attached to the proximal end of the handle 102. The knob 106 may be rotated to control the movement and/or function of one or more components associated with the catheter 100, such as for retraction of one or more catheter shafts or sheaths, or manipulation of an expandable member or other component carried at or near the distal end of the catheter shaft 104. Alternative structures may be substituted for the knob 106, such as one or more sliders, ratchet mechanisms, or other suitable control mechanisms known to those skilled in the art.

An inflation port 108 is located near the proximal end of the handle 102. The inflation port 108 is operatively connected to at least one inflation lumen that extends through the catheter shaft 104 to an expandable member 110 located near the distal end of the catheter shaft 104. The inflation port 108 is of any suitable type known to those skilled in the art for engaging an appropriate mechanism for providing an inflation medium to inflate the expandable member 110. For example, a suitable inflation mechanism is an Indeflator™ inflation device, manufactured by Guidant Corporation.

The catheter 100 is adapted to track a guidewire 112 that has been previously implanted into a patient and routed to an appropriate treatment location. A guidewire lumen extends through at least the distal portion of the catheter shaft 104, thereby providing the catheter 100 with the ability to track the guidewire 112 to the treatment location. The catheter 100 may be provided with an over-the-wire construction, in which case the guidewire lumen extends through the entire length of the device. Alternatively, the catheter 100 may be provided with a rapid-exchange feature, in which case the guidewire lumen exits the catheter shaft 104 through an exit port at a point nearer to the distal end of the catheter shaft 104 than the proximal end thereof.

Figure 2A:
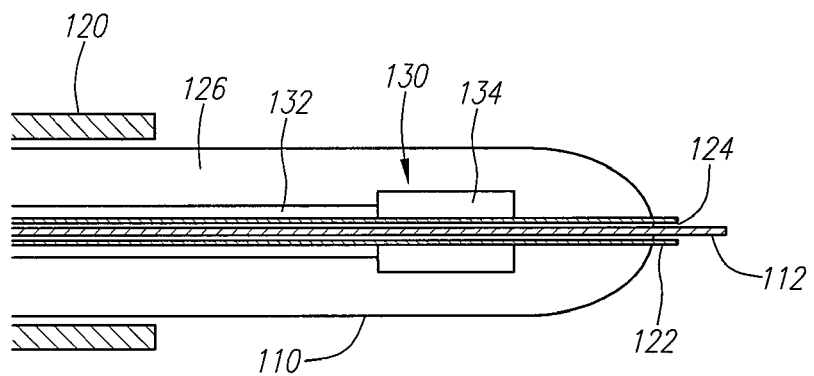
FIG. 2A is a cross-sectional view of an imaging device in accordance with the present invention.
Figure 2B:
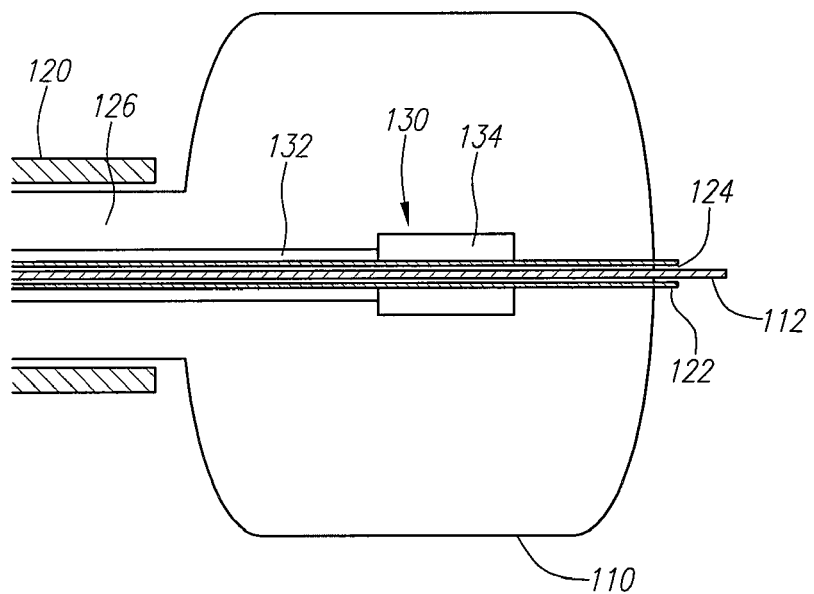
FIG. 2B is a cross-sectional view of the imaging device of FIG. 2A, showing an expandable member in its expanded state.

Turning next to FIGS. 2A-B, a first assessment mechanism is shown and described. The assessment mechanism is located at the distal end of a catheter 100, such as that illustrated in FIG. 1 and described above. The assessment mechanism shown in FIGS. 2A-B includes an imaging device that is used to provide two-dimensional or three-dimensional images of a vessel lumen or the hollow portion of an organ within the body of a patient, as described below.

The assessment mechanism includes the outer sheath 120 of the catheter shaft 104, which surrounds the expandable member 110. In the preferred embodiment, the expandable member 110 is an inflatable balloon. The expandable member 110 is attached at its distal end to a guidewire shaft 122, which defines a guidewire lumen 124 therethrough. The guidewire 112 extends through the guidewire lumen 124.

An imaging member 130 is contained within the expandable member 110. The imaging member 130 is supported by a shaft 132 that extends proximally to the handle 102, where it is independently controlled by the user. The imaging member shaft 132 is coaxial with and surrounds the guidewire shaft 124, but is preferably movable (e.g., by sliding) independently of the guidewire shaft 124. At the distal end of the imaging member shaft 132 is the imaging head 134. The imaging head 134 may be any mechanism suitable for transmitting and receiving a suitable imaging energy, such as ultrasonic waves. A typical imaging head 134 is an ultrasonic imaging probe. The structure and function of ultrasonic imaging probes are generally known to those skilled in the art, and is beyond the scope of the present application. The reader is instead directed to the abundant and available literature sources describing such devices.

The expandable member 110 is subject to expansion when a suitable expansion medium is injected into the expandable member through the inflation lumen 126. The inflation lumen 126, in turn, is connected to the inflation port 108 associated with the handle 102. FIG. 2A illustrates the expandable member 110 in its unexpanded (contracted) state, while FIG. 2B illustrates the expandable member 110 in its expanded state, such as after a suitable inflation medium is injected through the inflation port 108 and inflation lumen 126 into the expandable member 110.

To use the assessment mechanism illustrated in FIGS. 2A-B, the distal portion of the catheter is delivered to a treatment location within the body of a patient over the previously deployed guidewire 112. In a particularly preferred embodiment, the treatment location is the aortic heart valve, and the guidewire 112 is deployed through the patient's vasculature from an entry point in the femoral artery using, for example, the Seldinger technique. Deployment of the assessment mechanism is preferably monitored using fluoroscopy or other suitable visualization mechanism. Upon encountering the treatment location, the expandable member 110 is expanded by inflating the balloon with a suitable inflation medium through the inflation port 108 and the inflation lumen 126. The expandable member 110 engages the internal surfaces of the treatment location, such as the annular root of the aortic heart valve. Once the expandable member 110 is expanded, the imaging head 134 is activated and the imaging process is initiated. The imaging head 134 is preferably advanced, retracted, and rotated within the expandable member 110 as needed to obtain images in a variety of planes to yield a 360° three-dimensional image, or any desired portion thereof. Once the imaging process is completed, the expandable member 110 is deflated, and the assessment mechanism may be retracted within the catheter shaft 104. The catheter 100 is then removed from the patient.

Optionally, the inflation medium used to expand the expandable member 110 may comprise a material that enhances the ability of the imaging head 134 to generate images. For example, the inflation medium may facilitate enhanced acoustic transmission, reception, or it may reduce the incidence of scattering of the assessment signal. Such suitable inflation media include the following: acoustic gel, dielectric fluid, saline, and the like. These effects may be enhanced further by provision of a material or coating on the surface of the expandable member 110 that optimizes the imaging process. Such suitable materials and/or coatings include relatively dense materials such as metal, ceramic, high density polymers, and the like.

Turning next to FIGS. 3A-D, a plurality of physical assessment mechanisms are shown. Each physical assessment mechanism includes an expandable member 110 attached to a guidewire lumen 122 that extends through the catheter shaft 104 (see FIG. 1) and out of the distal end of the outer sheath (not shown). The guidewire lumen 122 is adapted to receive and track a guidewire 112 that has been previously deployed through the vasculature of a patient to the treatment location. In the embodiments illustrated, the treatment location is the aortic valve annulus 600. It should be recognized, however, that other treatment locations are possible, and that assessment information may be obtained for any suitable vessel lumen or hollow portion of an organ within the body of a patient.

Figure 3A:
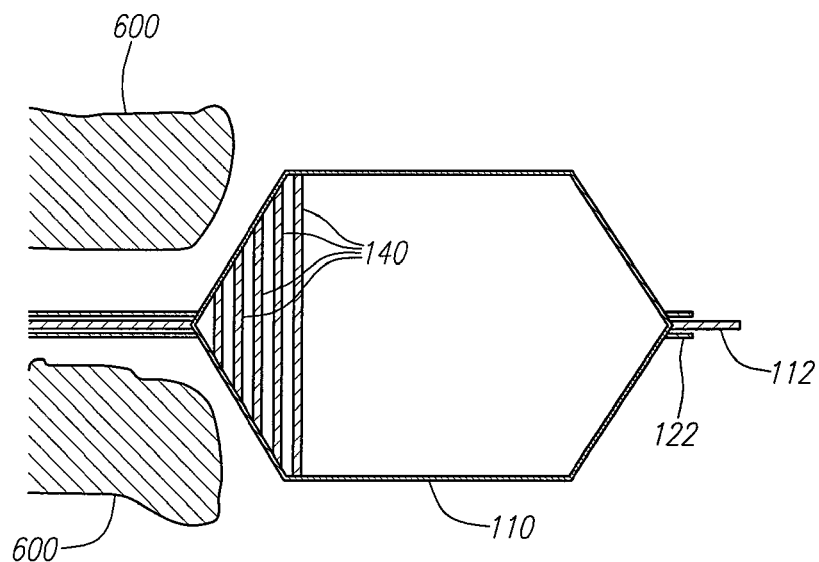
FIGS. 3A-C are side views of physical assessment members in accordance with the present invention.
Figure 3B:
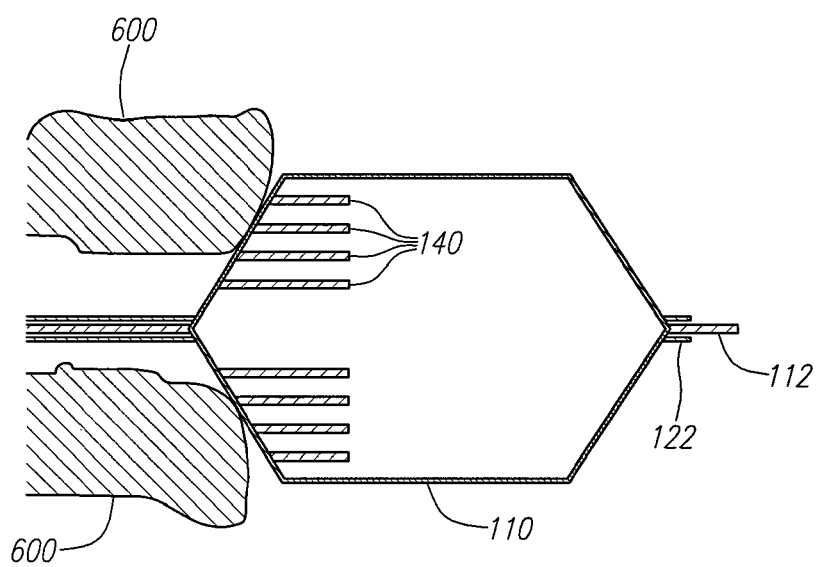

In FIG. 3A, the expandable member 110 includes a plurality of vertically oriented markers 140 that are located at spaced intervals extending along the tapered distal end of the expandable member 110. In FIG. 3B, the expandable member 110 includes a plurality of horizontally oriented markers 140 that are located at spaced intervals extending along the tapered distal end of the expandable member 110. In each of the embodiments, the markers 140 are preferably formed of a radiopaque material that may be embedded within the expandable member 110 or attached to the surface of the expandable member 110. The radiopaque markers 140 are thereby visible under fluoroscopy. In addition, because the markers 140 are indexed, the location of each marker indicates a particular size parameter. For example, as the tapered distal end of the expandable member 110 enters the aortic annulus 600, its forward motion is eventually stopped as the expandable member 110 engages the annulus 600. The point at which the expandable member 110 engages the annulus 600 will correspond with a particular one (or more) of the markers 140 located on the tapered distal end of the expandable member. This information may then be translated into an effective diameter, area, volume, or other physical measurement for the patient's aortic annulus 600 (or other measured lumen or hollow portion of an organ).

Figure 3C:
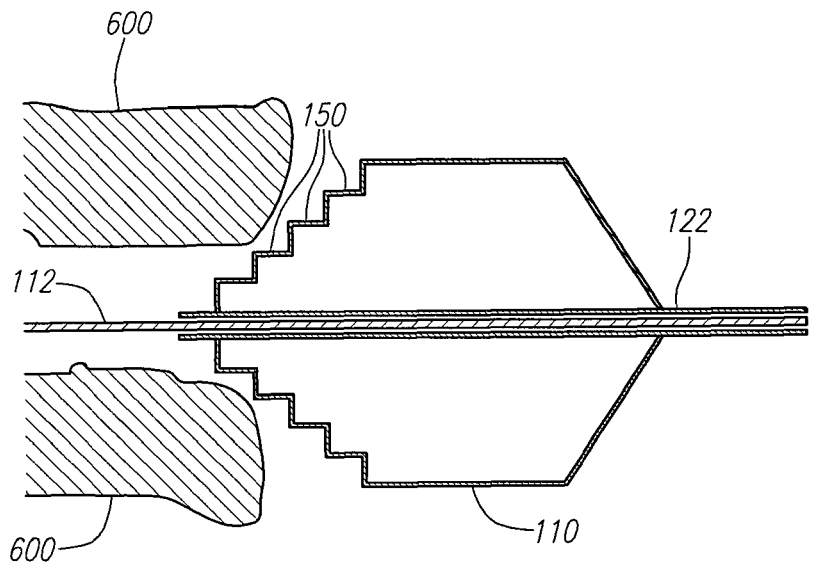

FIG. 3C illustrates another embodiment of the physical assessment member in which the expandable member 110 includes a plurality of graduated steps 150 formed on the distal portion of the expandable member 110. As with the previous embodiments shown in FIGS. 3A-B and described above, the graduated steps 150 are indexed. Accordingly, as the expandable member 110 engages the aortic annulus (or other lumen or hollow portion of an organ), the particular step 150 (or steps) upon which the engagement occurs will determine a size parameter (e.g., diameter, area, volume, etc.) for the annulus. The engagement step 150 is able to be visualized under fluoroscopy.

Figure 3D:
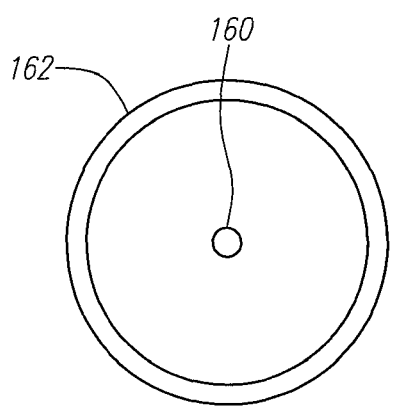
FIG. 3D is an end view of one of the physical assessment members of FIGS. 3A-C, illustrating an alignment mechanism.

FIG. 3D shows a schematic representation of an alignment device that may be used to ensure proper alignment of the expandable member 110 relative to the target location within the body of the patient. The alignment device includes a first radiopaque marker 160 in the shape of a dot that is attached to either the distal end or proximal end of the expandable member 110 surrounding the guidewire tube 122. The alignment device also includes a second radiopaque marker 162 in the shape of a ring that is attached to the opposite end of the expandable member from the end upon which the first marker 160 is attached. The ring-shaped marker 162 is also centered around the guidewire tube 122. The alignment device is operated by visualizing each of the first marker 160 and the second marker 162 under fluoroscopy. When the first marker 160 is centered within the second marker 162 as the expandable member 110 is viewed through its longitudinal axis, as shown in FIG. 3D, the user is assured that the expandable member 110 is normal to the fluoroscope field. This position is then used to ensure proper alignment with the target location within the body of the patient.

It is contemplated that other shapes, sizes, and orientations of the first marker 160 and second marker 162 are possible while still obtaining the advantages provided by the alignment mechanism. These advantages are obtained by detecting the position of the expandable member 110 through visualization of a pair of markers 160, 162 located at known positions on the body of the expandable member 110. The relative positions of the markers 160, 162 provide the needed alignment information to determine the position of the expandable member 110.

Turning next to FIGS. 4A-G, an assessment mechanism includes an electronic mapping construction that is attached to, or embedded within, the expandable member 110. The electronic mapping construction includes a plurality of electrical conductors 170 that form a plurality of circuits that are connected to a source of electrical energy by a primary conductor 172 that extends proximally from the expandable member 110 to the handle 102 of the catheter 100. A suitable source of electrical energy may be a battery located on the handle 102 or other electrical source that is accessible by the primary conductor 172.

An electric voltage or current is applied to the electrical conductors 170 by way of the primary conductor 172. Preferably, this is done after the expandable member 110 is expanded to engage the internal surface of the target location under investigation. Upon application of the electric load, the voltage or current created in the circuits making up the electronic mapping construction create electrical signals with one another in the form of a measurable capacitance, resistance, inductance, or reactivity. Accordingly, when measurements of these properties are made between pairs of circuits, the measured values are used to determine information relating to the relative spacing between the circuits. The spacing information is then processed to determine the size, shape, and topography of the target location over the entire electronic mapping construction. In a preferred embodiment, the catheter is connected to an electronic console that is able to process the signals in the manner described above and then display a 2 or 3 dimensional image of the topography of the site, depict the compliance of the tissue, thrombus, calcification, prior implant or other structures as well as pressure gradients, flow, orifice areas, and the like. The user would thereby be provided with sufficient information to predict the performance, safety, and efficacy of a prosthetic (or other) device to be implanted in the assessed region.

Figure 4A:
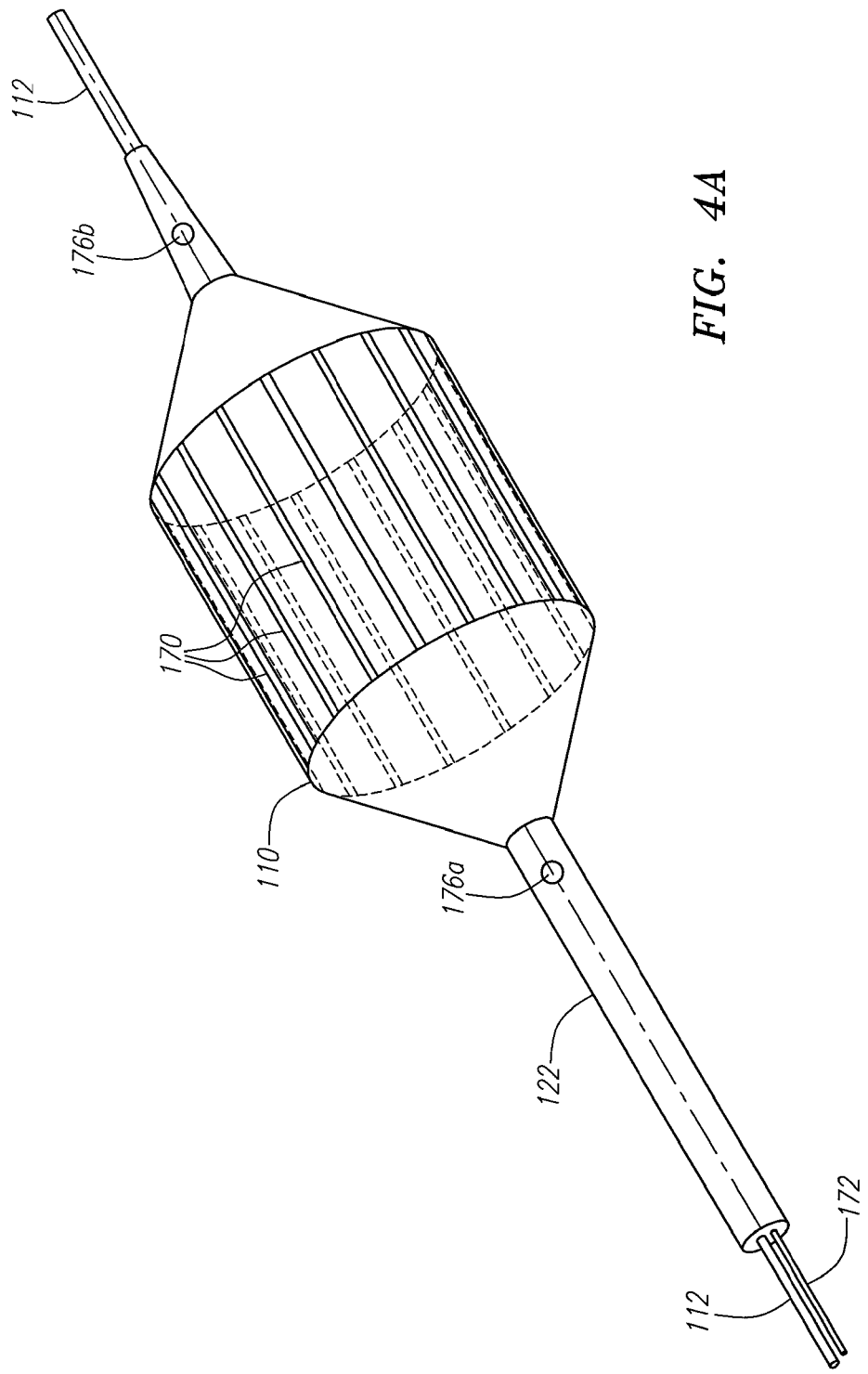
FIG. 4A is a perspective view of an electronic mapping member in accordance with the present invention.
Figure 4B:
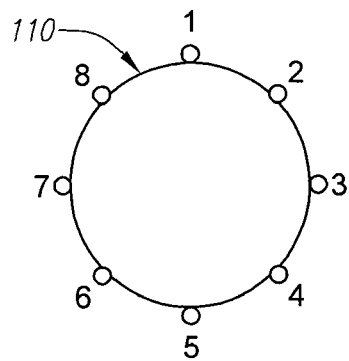
FIGS. 4B-D are schematic representations illustrating several relative orientations of conductors carried by the electronic mapping member of FIG. 4A.
Figure 4C:
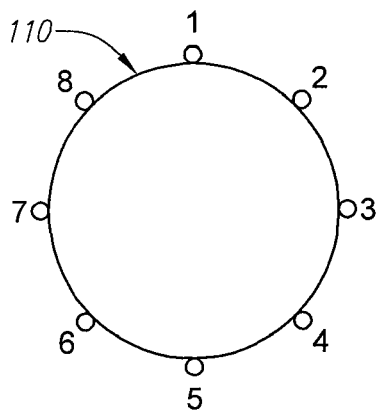
Figure 4D:
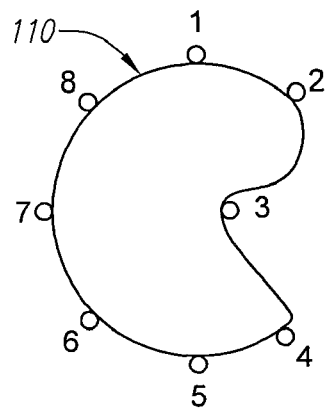

A few simple examples shown schematically in FIGS. 4B-D will illustrate this method. Each of the examples illustrates an orientation that may be encountered by the expandable member 110 having, for example, eight longitudinal conductors extending axially along the length of the expandable member. Measurements are taken by measuring an electrical signal generated between each conductor relative to each of the other conductors, until a complete set of signals is collected. In the first example, shown in FIG. 4B, a relatively small diameter, generally cylindrical lumen is encountered. In this case, the conductors 1-8 are in relatively close proximity to one another, and the spacing is generally uniform between pairs of relatively spaced conductors. This orientation will generate a first measured capacitance between each pair conductors that corresponds with the relative orientations between the conductors. In the second example, shown in FIG. 4C, a larger diameter, generally cylindrical lumen is encountered. In this case, the conductors 1-8 are spaced further apart from one another than in the preceding case, although the spacing remains relatively uniform between pairs of relatively spaced conductors. This orientation will generate a second measured capacitance between each pair of conductors that corresponds with the relative orientations between the conductors. In the third example, shown in FIG. 4D, a lumen having an irregular diameter is encountered. In this example, the distance between conductors 1 and 5 is different from the distance between conductors 3 and 7, thereby creating a difference in the measured capacitance between these pairs of conductors that would indicate the irregularity.

Figure 4E:
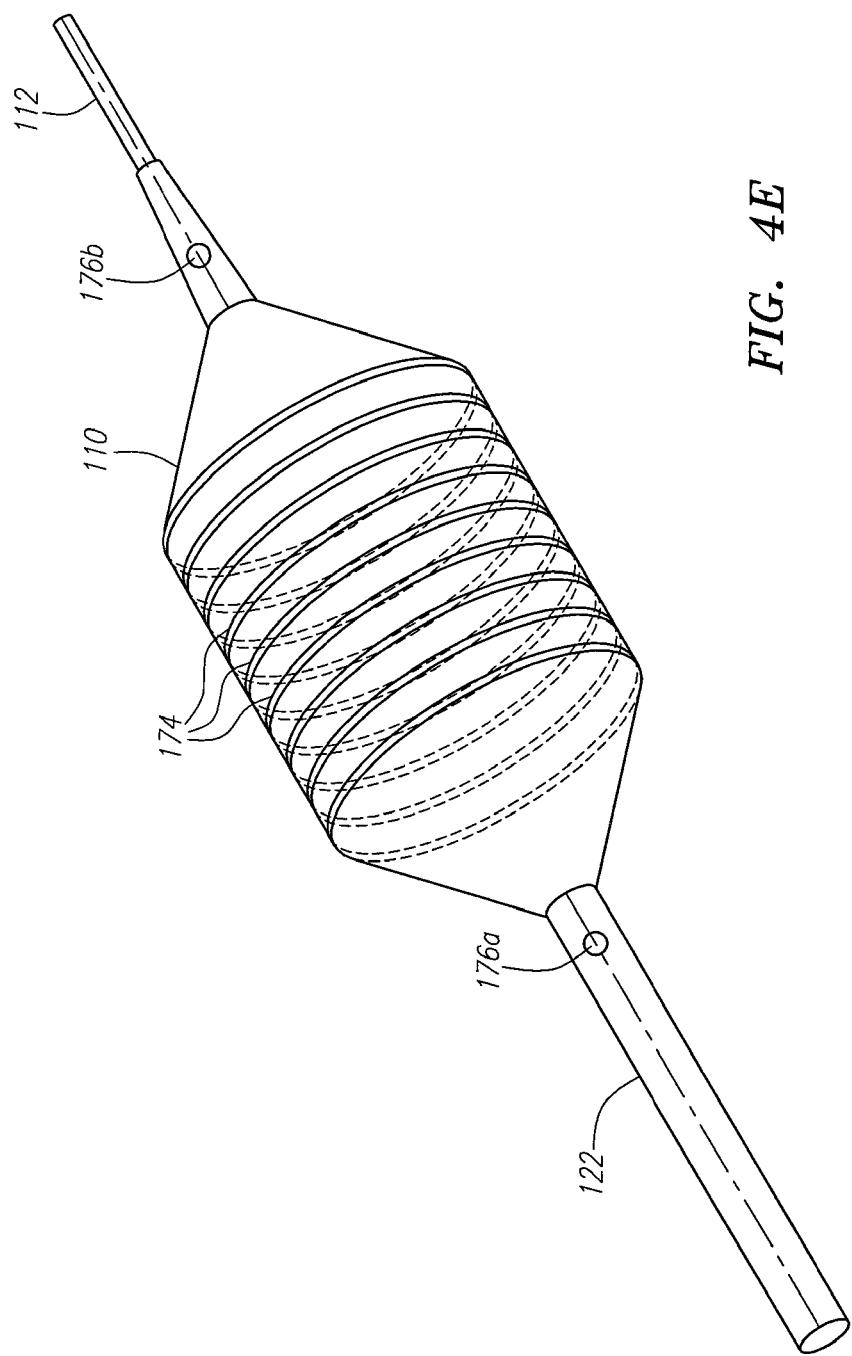
FIGS. 4E-G are alternative embodiments of electronic mapping members in accordance with the present invention.
Figure 4F:
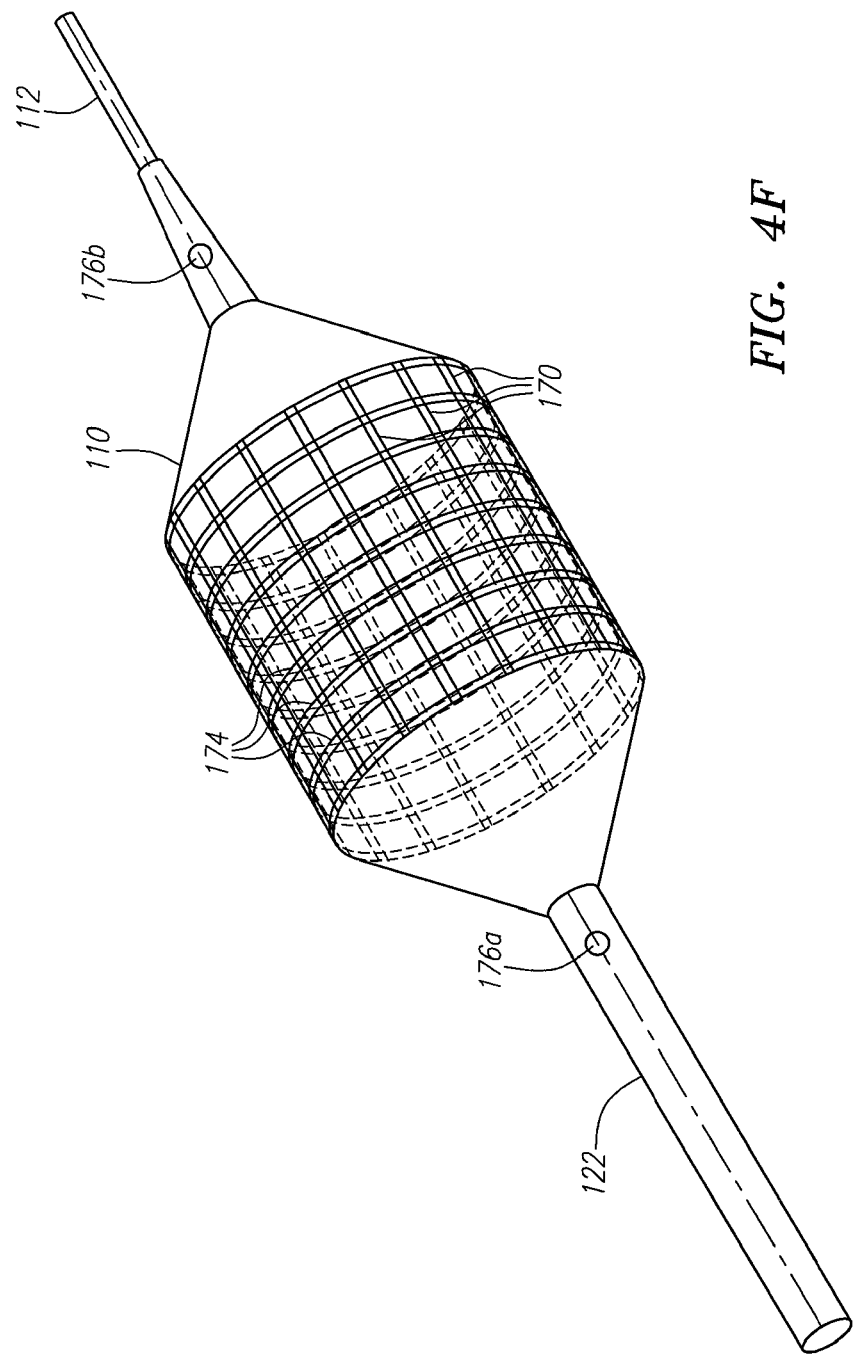
Figure 4G:
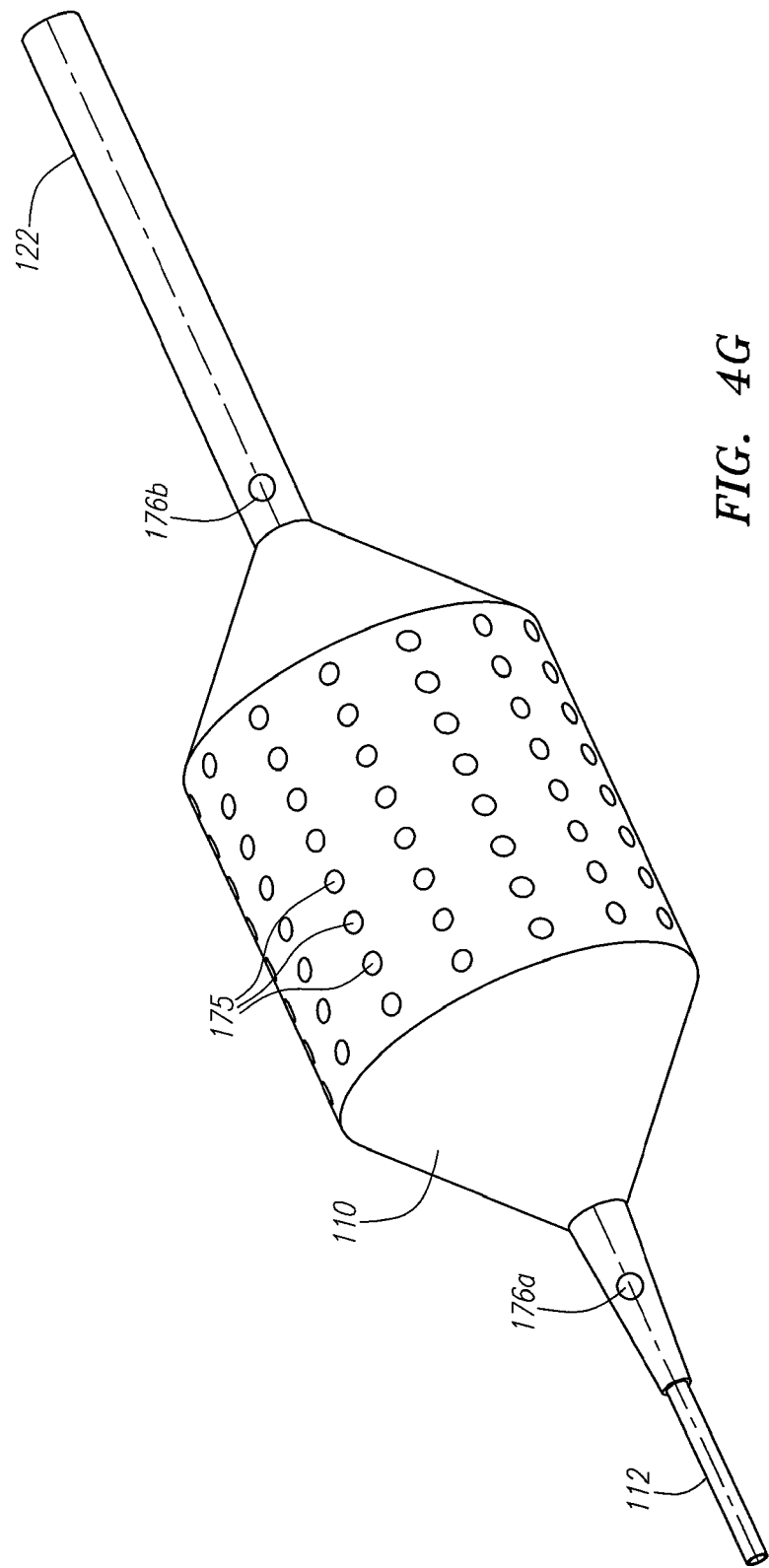

FIG. 4E shows an alternative embodiment of the electronic mapping construction in which a second set of conductors 174 forming a second set of circuits is formed on the surface of or embedded within the expandable member 110. The second set of conductors 174 are oriented generally transversely to the first set of conductors 170 shown in the prior embodiment in FIG. 4A. FIG. 4F shows yet another alternative embodiment that includes both sets of conductors 170, 174, in which the first set of conductors 170 is generally nested within the second set of conductors 174. The electrical grid provided by the combined sets of conductors is capable of creating a three-dimensional topographical mapping of the entire treatment location to which the expandable member 110 is engaged. Finally, FIG. 4G shows another alternative embodiment in which the conductors 175 are distributed at points around the periphery of the expandable member 110, rather than linear conductors. Like the prior embodiments, the embodiment shown in FIG. 4G is also able to create a three-dimensional topographical mapping of the treatment location.

In each of the electronic mapping construction embodiments shown above, a pair of pressure sensors 176a, 176b is provided. A first pressure sensor 176a is preferably located on the guidewire tube 122 at or near the proximal end of the expandable member 110, while the second pressure sensor 176b is preferably also located on the guidewire tube 122, but at or near the distal end of the expandable member 110. The pressure sensors 176a, 176b are adapted to provide pressure measurements to indicate fluid flow (or the absence thereof) in the vessel or organ. For example, when the expandable member is fully expanded, it will preferably completely dilate a stenotic area (such as an aortic valve) and occlude fluid flow through the vessel. Occlusion may be determined through pressure measurements on the proximal and distal sides of the expandable member 110.

Figure 5A:
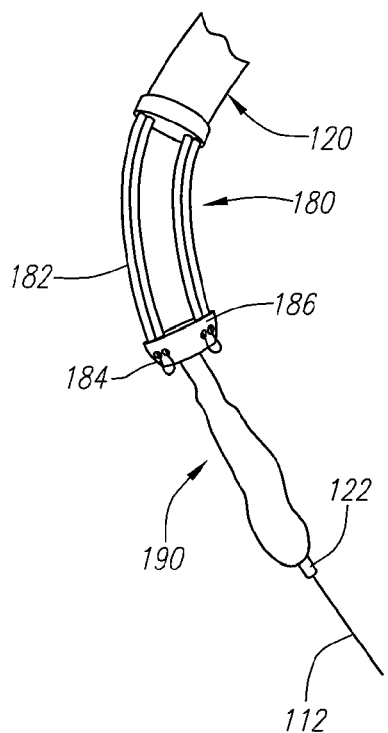
FIGS. 5A-C are perspective views of a multi-function catheter in accordance with the present invention.
Figure 5B:
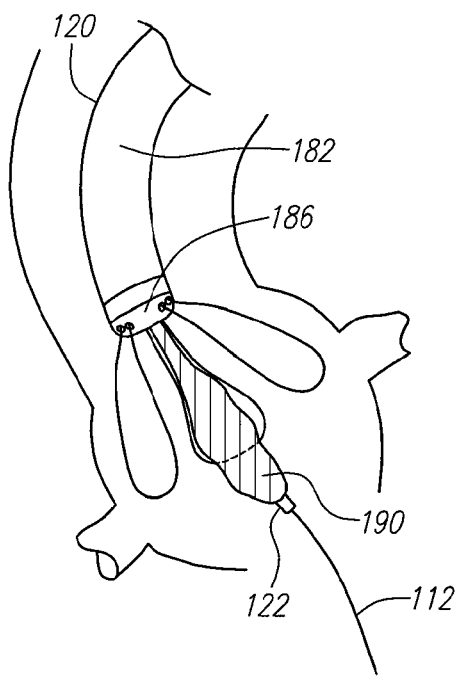
Figure 5C:
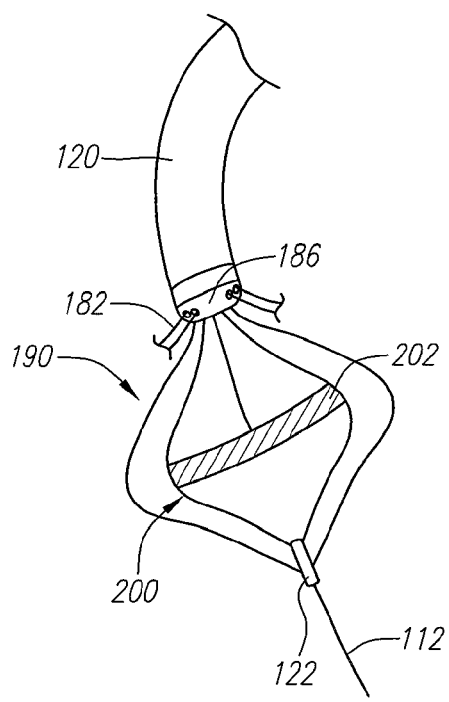

Turning next to FIGS. 5A-C, a multi-function catheter construction is shown. The multi-function catheter construction includes an alignment mechanism 180 for proper positioning, an exterior balloon 190 for performing a valvuloplasty procedure, and an inner expandable member 200 for determining one or more physical parameters of the target location. In alternative embodiments, the valvuloplasty balloon 190 is located on the interior of the measuring balloon 200.

FIG. 5A illustrates the distal portion of the multi-function catheter prior to deployment. The alignment mechanism 180 extends out of the distal end of the outer sheath 120 of the catheter. The alignment mechanism includes a plurality of alignment wires 182 that are attached at their proximal ends to the distal end of the outer sheath 120. The distal ends of the alignment wires 182 extend out of a plurality of holes 184 formed on an alignment cap 186. Each alignment wire 182 is preferably in the form of a wire loop. In the preferred embodiment, three alignment loops 182 are present. The valvuloplasty balloon 190 extends distally of the alignment cap 186. The guidewire 112 extends from the guidewire 122 to which the valvuloplasty balloon 190 is attached.

FIG. 5B illustrates the advancement of the alignment loops 182, which is caused by causing relative motion between the distal end of the outer sheath 120 and the alignment cap 186 toward one another, thereby causing the alignment loops 182 to advance distally relative to the alignment cap 186. As the alignment loops 182 advance, they are biased outward (i.e., radially expand). In the preferred method for treating an aortic heart valve, the catheter is then advanced such that the alignment loops 182 become lodged in the sinus located behind the native valve leaflets, thereby fixing the alignment mechanism 180 in place relative to the aortic valve annulus. This fixation also fixes the location of the remainder of the catheter 100 in place relative to the valve annulus. Tactile feedback and visual confirmation will assure that the alignment loops 182 have positioned the catheter properly, thereby placing the valvuloplasty balloon 190 and expandable member 200 directly in line with the aortic valve annulus.

In FIG. 5C, the valvuloplasty balloon is shown in its expanded state, which is achieved by injecting a suitable inflation medium through an inflation lumen provided in the catheter shaft 104. The valvuloplasty balloon 190 is preferably inflated to enlarge to a prescribed diameter larger than the estimated annulus diameter, thereby performing the function of a conventional valvuloplasty. The valvuloplasty balloon 190 is then deflated.

The inner expandable member 200 is then inflated to a measured volume and pressure. The inner expandable member 200 is preferably formed of a non-compliant material, although a compliant material is used in alternative embodiments. In the preferred embodiment shown in the Figures, a resistance strip 202 is attached to (e.g., printed onto) the outer surface of the expandable member 200. The resistance strip 202 is used to measure an increase in the size and resistance of the expandable member 200, which information is then correlated to a corresponding circumferential length or volume. This circumferential length (or volume) measurement is then used to determine the annulus size for the given pressure. Accordingly, both size and compliance of the annulus are able to be determined. In alternative embodiments, the relationship between the internal pressure of the expandable member 200 and its measured or correlated volume are used to measure the compliance of the tissue (or other environment) engaged with the external surface of the expandable member 200.

It is worth noting that although the foregoing description is based upon use of the multi-function catheter in the assessment of an aortic valve, the device may be used to obtain assessment information of other vessels and organs in the body of a patient as well. Moreover, the alignment mechanism 180 described for use with the multi-function catheter may be incorporated onto other devices, such as a delivery device used to deliver a prosthetic heart valve to a treatment location.

The preferred embodiments of the inventions that are the subject of this application are described above in detail for the purpose of setting forth a complete disclosure and for the sake of explanation and clarity. Those skilled in the art will envision other modifications within the scope and spirit of the present disclosure. Such alternatives, additions, modifications, and improvements may be made without departing from the scope of the present inventions, which is defined by the claims.

What is claimed is:

1. A method of assessing inner surfaces of a vessel lumen, or inner surfaces of a hollow portion of an organ, in a body of a patient, the method comprising:
shaping an assessment member into contours of the inner surfaces by pressing the assessment member outward against the inner surfaces;
dilating the inner surfaces by moving the assessment member outward against the inner surfaces;
measuring the outward movement of the assessment member with an imaging device contained within the assessment member;
detecting the shaped contours of the assessment member with the imaging device;
assessing compliance of the inner surfaces based on the measured outward movement of the assessment member; and
assessing the peripheral shape of the dilated inner surfaces based on the detected shaped contours of the assessment member.

2. The method of claim 1 wherein the assessment member is moved outward against the inner surfaces by deflecting the assessment member under pressure applied from within the assessment member.

3. The method of claim 2 wherein the assessment member is moved outward against the inner surface by expanding the assessment member.

4. The method of claim 3 wherein the assessment member is an inflatable balloon and is expanded by introducing an expansion medium into the balloon.

5. A method of assessing a body of a patient at inner surfaces of a vessel lumen, or inner surfaces of a hollow portion of an organ, for placement of an implant in a target area surrounded by the inner surfaces, comprising:
shaping an assessment member into contours of the inner surfaces about the periphery of the target area by pressing the assessment member outward against the inner surfaces;
dilating the target area against resistance of the inner surfaces by moving the assessment member outward against the inner surfaces;
measuring the outward movement of the assessment member and the shaped contours of the assessment member with an imaging device contained within the assessment member;
assessing the resistance of the inner surfaces, the dilation of the target area, and a dilated peripheral shape of the target area based on the measured outward movement of the assessment member and the measured shaped contours of the assessment member.

6. The method of claim 5 further comprising the steps of selecting an implant with reference to the assessed resistance, dilation, and peripheral shape; removing the assessment member form the target area; and subsequently placing the selected implant in the target area.

7. The method of claim 5 wherein the assessment member is moved outward against the inner surfaces by deflecting the assessment member under pressure applied from within the assessment member.

8. The method of claim 7 wherein the assessment member is moved outward against the inner surface by expanding the assessment member.

9. The method of claim 8 wherein the assessment member is an inflatable balloon and is expanded by introducing an expansion medium into the balloon.

* * * * *